(12) United States Patent
Burger et al.

(10) Patent No.: US 7,080,666 B2
(45) Date of Patent: Jul. 25, 2006

(54) SYSTEM FOR TREATING FLUIDS

(75) Inventors: Josef Burger, Schmidgaden (DE); Oliver Heel, Amberg (DE); Astrid Lohf, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/944,746

(22) Filed: Sep. 21, 2004

(65) Prior Publication Data

US 2005/0139262 A1 Jun. 30, 2005

Related U.S. Application Data

(63) Continuation of application No. PCT/DE03/00934, filed on Mar. 20, 2003.

(30) Foreign Application Priority Data

Mar. 21, 2002 (DE) ................................ 102 12 611

(51) Int. Cl.
*F16K 1/00* (2006.01)
*F16K 9/00* (2006.01)
(52) U.S. Cl. ........................ 137/884; 137/341; 251/367
(58) Field of Classification Search ................ 137/340, 137/341, 884, 269, 270; 222/146.1, 146.2, 222/146.6; 251/367
See application file for complete search history.

(56) References Cited

U.S. PATENT DOCUMENTS 4,082,324 A * 4/1978 Obrecht .................... 285/124.5
4,714,091 A 12/1987 Wagner
5,605,179 A 2/1997 Strong, Jr. et al.
5,996,369 A * 12/1999 Hirota ........................ 62/324.6
6,102,068 A * 8/2000 Higdon et al. .............. 137/341
6,102,668 A * 8/2000 Kawaguchi et al. ...... 417/222.2
6,286,721 B1 * 9/2001 Pellegrini ................. 222/129.1
2002/0000257 A1 * 1/2002 Mead et al. ................. 137/884
2002/0007858 A1 1/2002 Xu et al.
2002/0134445 A1 9/2002 Eidsmore et al.
2002/0186666 A1 12/2002 Hassel et al.

FOREIGN PATENT DOCUMENTS

| DE | 694 27 980 T2 | 10/1995 |
|----|----|----|
| DE | 100 38 288 C2 | 2/2002 |
| JP | 2003056732 A | 2/2003 |
| WO | WO 99/45302 | 9/1999 |
| WO | WO 01/36085 A1 | 5/2001 |

* cited by examiner

*Primary Examiner*—A. Michael Chambers
(74) *Attorney, Agent, or Firm*—Sughrue Mion, PLLC

(57) ABSTRACT

A system for processing fluids, the system having a unit (1) for supplying and discharging the fluids. The unit has a plurality of fluid lines terminating in a plurality of fluid ports, an assembly side (3) with the plurality of fluid ports terminating therein. The system also has at least one device (4) in which at least one of the fluids is processed. The at least one device is operable to be mounted on the assembly side and further operable to be coupled to the plurality of fluid ports (11, 12, 13, 14). The at least one device has a plurality of components (29, 30, 31) performing a plurality of functions related to the processing of the at least one of the fluids. The components are mounted on the assembly side in superimposed planes. The fluid ports supply and discharging the fluids to and from the components. The fluid ports have different lengths and extend from the assembly side (3) to at least one of the components (29, 30).

13 Claims, 2 Drawing Sheets

SYSTEM FOR TREATING FLUIDS

This is a Continuation of International Application PCT/DE03/00934, with an international filing date of Mar. 20, 2003, which was published under PCT Article 21(2) in German, and the disclosure of which is incorporated into this application by reference.

FIELD AND BACKGROUND OF THE INVENTION

The invention relates to a system for supplying and discharging fluids intended for processing.

A conventional system is disclosed in WO 99/45302 (corresponding to U.S. 2002134445A1), in which different devices for processing fluids, e.g., valves, pressure transducers or flow controllers, are mounted on an assembly side of a unit. The unit is used for supplying fluids to the device or for discharging the fluids from the device. For this purpose, the fluid supply and discharge unit has fluid lines that terminate at fluid ports on the assembly side, such that the devices for processing the fluid couple to the associated fluid ports when mounted.

In another conventional system disclosed in WO 01/36085 (corresponding to U.S. 2002186666A1), process modules that perform module-specific functions in connection with the processing of the fluids are mounted end to end. These modules are interconnected via a data bus on the control side and a fluid bus on the fluid side. The fluid bus, like the data bus, may consist of bus segments within the process modules, such that the corresponding bus is composed of the bus segments when the process modules are mounted end to end. Alternatively, the process modules may be individually connected to an external fluid bus via associated adapters.

OBJECTS OF THE INVENTION

This disclosure teaches processing of fluids. In particular, the term processing includes analysis and/or synthesis of fluids, as well as associated secondary functions, e.g., pumping, heating/cooling, filtering, etc. While the term fluids is used, a skilled artisan will know that the techniques are applicable equally to liquids, gases and/or solids transported by carrier fluids.

Different functions that must be performed to process the fluids are often closely interrelated. One example is the mixing of two educts while simultaneously removing the reaction heat by means of a heat transfer fluid. An object of the invention is to provide an optimal structure of a system for processing fluids so that the fluid processing functions can be performed efficiently.

SUMMARY OF THE INVENTION

Preferably to achieve these objects, there is provided a system for processing fluids, the system including a unit for supplying and discharging the fluids. The unit has a plurality of fluid lines terminating in a plurality of fluid ports, an assembly side with the plurality of fluid ports terminating therein and at least one device in which at least one of the fluids is processed. The at least one device is operable to be mounted on the assembly side and further operable to be coupled to the plurality of fluid ports. The at least one device has a plurality of components performing a plurality of functions related to the processing of the at least one of the fluids. The components are mounted on the assembly side in superimposed planes. The fluid ports supply and discharging the fluids to and from the components. The fluid ports have different lengths and extend from the assembly side to the components.

Since the system for processing fluids consists of components that perform different functions in connection with the processing of the fluids and these components are arranged in different planes, a generally compact sandwich-type structure of the system is obtained. The components with the different functions can be modularly assembled as needed, providing high flexibility in the combination of the different functions. Because of the arrangement in superimposed planes, immediately adjacent components have large contact areas, which enables particularly effective heating or cooling of the individual components.

For example, a component performing the function of a reactor and an additional component performing the function of a heat exchanger can be arranged in directly adjacent planes, such that the heat exchanger has a large contact area with the reactor and can effectively cool the reactor. Furthermore, the individual components can be optimally designed for their respective functions, e.g., they can be manufactured from a material suitable for the corresponding application, e.g., high-grade steel, such that different components can be made from different materials. Within the individual components, however, a mixture of materials and the attendant problems, e.g., sealing problems, are avoided.

The fluidic connection between the components in the individual planes and the fluid lines within the fluid supply and discharge unit is effected by fluid ports of different lengths, which extend from the assembly side of the unit to the corresponding component. This eliminates, in particular, the need for any hose connections from the fluid supply and discharge unit to the individual components. The components located in the planes closer to the assembly side of the unit preferably have passageways for the fluid ports of the fluid lines that serve to supply and discharge the fluids to and from the components that are farther remote from the assembly side. Since in contrast to external hose ports, the fluid ports extend within the composite of the superimposed components, the fluids conducted through them are kept at the same temperature as the components, irrespective of external temperature fluctuations.

The system according to the invention can have a plurality of fluid processing devices, each with different components. To achieve a largely uniform structure of the system according to the invention, the functions performed by the components can be divided into different classes, e.g., heat supply and removal, fluid distribution and the actual fluid processing, and different planes can be specified for different function classes. If, for example, the components for heat supply and removal, e.g., heat exchangers, are always located in a specific plane, the corresponding fluid ports for the heat transfer fluid in the fluid supply and discharge unit can be uniformly configured to terminate in this specific plane. The fluid ports for the heat transfer fluid can also have a larger flow cross-section than other fluid ports. If a certain function class is not present in individual fluid processing devices, e.g., because there is no need to supply or remove heat, a functionless substitute spacer component may be provided instead of the component that is not required. This spacer component ensures that the remaining components are located in their assigned planes.

Preferably, the components mounted one on top of the other on the assembly side of the unit consist of a lower fluid heating/cooling component, a center fluid distribution component and an upper individual fluid processing component.

The fluid heating/cooling component is operable to bring the fluid in the adjacent components to the right temperature, while the fluid distribution component serves to individually supply and discharge the fluid to and from the fluid processing component.

The fluid heating/cooling component can be a standard component, e.g., a heat exchanger, whereas the fluid processing component is an individual component, e.g., a reactor, which performs a specific fluid processing function. The fluid distribution component ensures a fluidic connection between the standard fluid ports of the unit for supplying and discharging the fluids and the ports of the individual components.

To enable not only the fluid supply and discharge by the unit to which the fluid processing devices are mounted but also a direct transfer of fluids from one component to an immediately adjacent component, these components preferably each have fluid fittings, which establish a fluidic connection between the two components once the components are assembled.

Preferably, at least some of the components are made as plates, which have channel-like recesses to conduct the fluids on one or both sides, which are parallel to the assembly side. The channel-like recesses are covered, respectively, by the immediately adjacent component, possibly with the interposition of a sealing layer. The sealing layer may be omitted if only one of the opposite sides of two adjacent components has channel-like recesses. Otherwise, the sealing layer separates the fluids in the adjacent components. For example, the fluid in the one component can be a heat transfer fluid to heat or cool the fluid in the other component.

As already mentioned, a plurality of similar or different devices for fluid processing may be mounted to a single fluid supply and discharge unit. Preferably, a plurality of fluid supply and discharge units can moreover be interconnected. For this purpose, the units have connection sides on which they can be interconnected to form a fluid bus by connecting their fluid lines. To ensure that the units are securely connected, they preferably each have locking devices to mechanically interlock with the respectively adjacent units.

BRIEF DESCRIPTION OF THE DRAWINGS

The invention will now be described in greater detail with reference to the drawing figures in which.

DETAILED DESCRIPTION OF THE PREFERRED EMBODIMENTS

Figure 1:
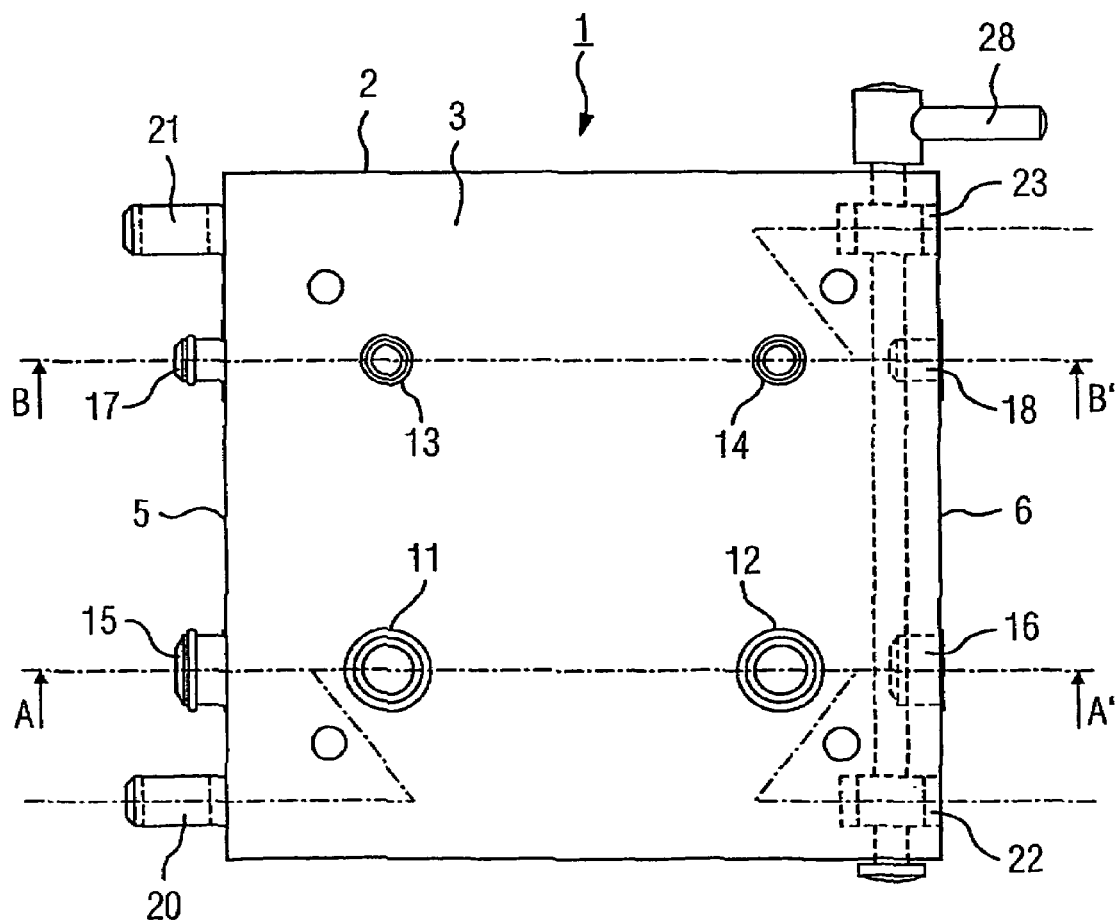
FIG. 1 shows the assembly side of an exemplary embodiment of the fluid supply and discharge unit.

FIG. 1 shows the assembly side of an exemplary embodiment of the fluid supply and discharge unit. As shown in FIG. 1, the fluid supply and discharge unit 1 includes a frame 2 with an assembly side 3 for mounting a fluid processing device 4. Fluid lines 7, 8, 9 and 10 extend in the interior of the unit 1 between two parallel connection sides 5 and 6. The two parallel connection sides 5 and 6 are perpendicular to the assembly side 3.

The fluid lines terminate at fluid ports 11, 12, 13 and 14 on the assembly side 3. On the other end, the fluid lines terminate at fluid ports 15, 16, 17 and 18 on the connection sides 5 and 6. The fluid lines 7 and 8 carry a heat transfer fluid and have a larger flow cross section than the other fluid lines 9 and 10. Likewise the fluid ports 11, 12, 15 and 16 that are associated with fluid lines 7 and 8 have a larger flow cross section than the fluid ports 13, 14, 17 and 18 that are associated with the fluid lines 9 and 10.

Insulating bodies 19 surround the fluid lines 7–10 in the interior of the unit 1 to keep the temperature in the fluid lines constant. The insulating bodies 19 can be sponge-like so that they can absorb escaping fluids in the event that leaks develop in the fluid lines 7–10.

On the connection sides 5 and 6, another unit of the same type may be connected, such that the fluid lines in the respectively adjacent units are interconnected via their fluid ports on the connection sides. The fluid lines and the associated fluid ports in the adjacent units complement each other to form a fluid bus. In this manner, a plurality of units 1 can be connected end to end.

To ensure that the units are properly aligned and are interconnected in a secure manner, they each have a locking device to mechanically interlock with the adjacent unit. In the exemplary embodiment shown, the locking device include pins 20 and 21 on the one connection side 5. These pins from the unit that is part of the exemplary embodiments fit into locating holes 22 and 23, respectively on the connection side 6 of the adjacent unit (not shown).

The pins 20 and 21 each have a lateral recess 24 or 25. In a corresponding position in the area of the locating holes 22 and 23 a cam 26 or 27 is rotatably supported by means of a lever 28. In a first rotational position the cam 26 or 27 unblocks the path through the locating hole 22 or 23 whereas in a second rotational position it locks the pin 20 or 21 within the locating hole 22 or 23.

Figure 2:
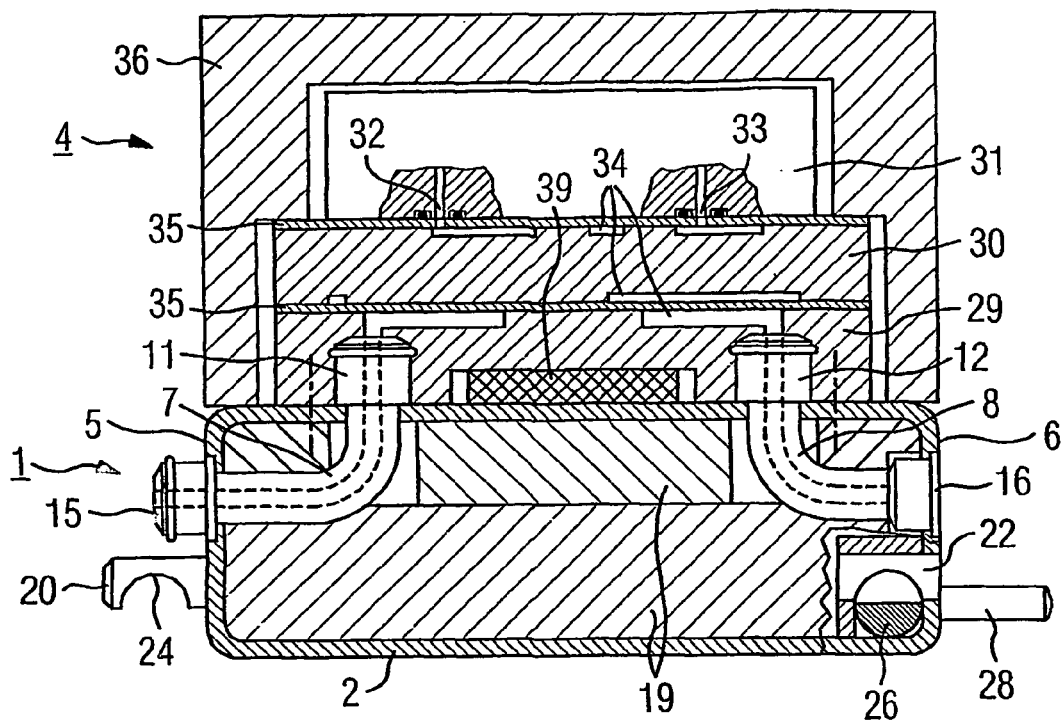
FIG. 2 shows a section taken along line A–A' in FIG. 1 of the fluid supply and discharge unit with a fluid processing device mounted thereto.
Figure 3:
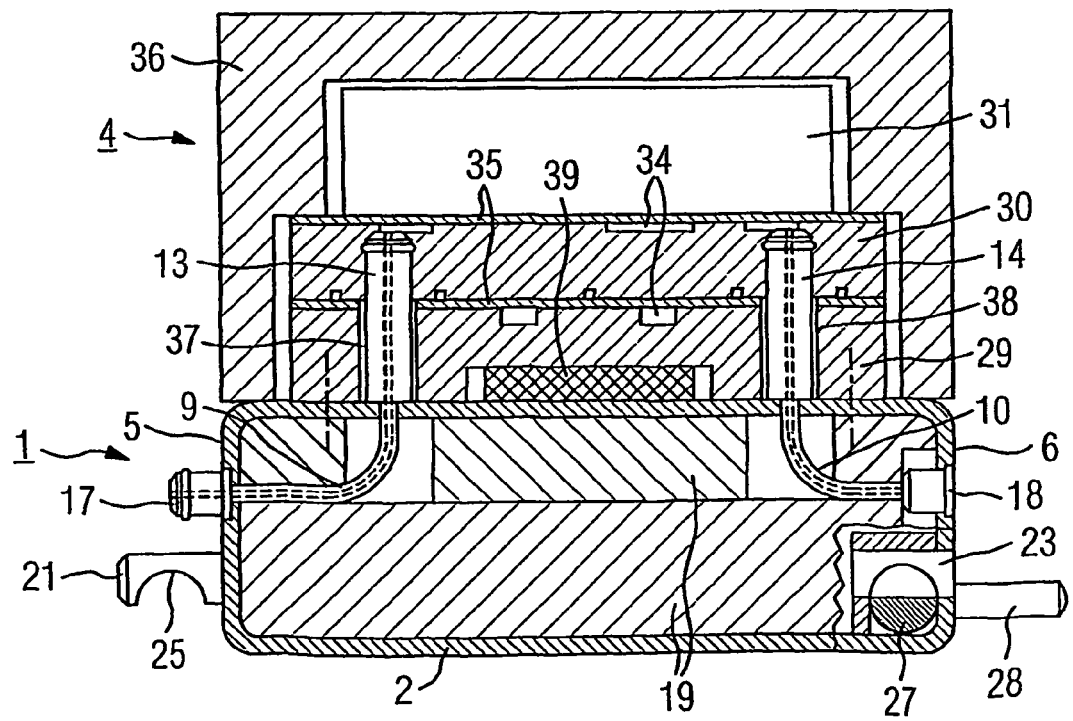
FIG. 3 shows a section taken along line B–B' in FIG. 1 of the fluid supply and discharge unit with the fluid processing device mounted thereto.

As shown in FIGS. 2 and 3, the device for fluid processing 4 includes a plurality of components 29, 30 and 31, which are mounted in superimposed planes on the assembly side 3 of the fluid supply and discharge unit 1. The components 29, 30 and 31 perform different fluid processing functions. In the exemplary embodiment shown, the component 29 is used for cooling or heating. For this purpose, the component 29 is supplied with a heat transfer fluid from the unit 1 via the fluid ports 11 and 12. On its side facing the unit 1, the component 29 further has a clearance for receiving an electrically operated heating device 39.

The component 30 distributes or transfers a fluid supplied or discharged to or from the component 31 via the fluid ports 13 and 14 in which the actual fluid processing is effected. The fluid is transferred between the adjacent components 30 and 31 via ports 32 and 33. These ports establish a direct fluidic connection between the two components 30 and 31 once the components 30 and 31 are mounted. The component 31, for example, could be a valve system, a pump, filter, mixer, reactor, delay unit, analyzer, etc.

Within the components 29, 30 and possibly also 31, the corresponding fluids are conducted in channel-like recesses 34, which are formed on the sides of the components 29 and 30 parallel to the assembly side 3 of the unit 1. These recesses are covered by the respectively adjacent components with the interposition of a sealing layer 35. Depending on whether the components 29, 30, 31 are to be brought to the same or different temperatures, the thermal conductivity of the sealing layers 35 is either high or low.

To minimize external influences, particularly temperature influences on the components 29, 30 and 31, the components are enclosed in an insulating material 36, which in this case is positioned over the components 29, 30 and 31 like a cap.

The fluid ports 11–14 formed on the assembly side 3 of the unit 1 to supply and discharge fluid to and from the components 29 and 30 which are arranged in the different planes have different lengths. These fluid ports extend from the assembly side 3 to the respective component 29 or 30. The lower component 29, which is closer to the assembly side 3, has passageways 37 and 38 for the longer fluid ports 13 and 14, which supply and discharge fluid to and from the superjacent component 29. As previously mentioned, the fluid is exchanged directly between the two components 30 and 31.

While the exemplary embodiment has four lines, a skilled artisan will know that more or less number of fluid lines can be provided. The fluid ports 11–18 can furthermore be made self-sealing to prevent fluids from escaping when components, e.g., 29, are removed or when interconnected units 1 are disconnected.

The fluid processing device 4 with its components 29, 30 and 31 may be supplied via unit 1 not only with fluids but also with data and power, as disclosed in the initially mentioned publication WO 01/36085. For this purpose corresponding data and power ports may be provided in addition to the fluid ports 11–18. Furthermore, the locking state of adjacent units 1 and/or the mounting state of the components 29–30 on the unit 1 may be monitored, e.g., electrically.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. A system for processing fluids, the system comprising:
    a unit for supplying and discharging the fluids, the unit further having:
    a plurality of fluid lines terminating in a plurality of fluid ports; and
    an assembly side with the plurality of fluid ports terminating therein; and
    at least one device in which at least one of the fluids is processed,
    the at least one device operable to be mounted on the assembly side and further operable to be coupled to the plurality of fluid ports,
    the at least one device having a plurality of components performing a plurality of functions related to the processing of the at least one of the fluids, the components being mounted on the assembly side in superimposed planes,
    the fluid ports supplying and discharging the fluids to and from the components, the fluid ports having different lengths and extending from the assembly side to the components,
    wherein at least one component which lies in one of the superimposed planes closer to the assembly side contains at least one passageway for at least one of the fluid ports for supplying and discharging fluids to and from a second component farther away from the assembly side.

2. The system of claim 1 wherein a subset of the plurality of superimposed planes are associated with a class of functions, the subset of planes including a subset of components performing the class of functions.

3. The system of claim 1 having at least one functionless substitute spacer component where no function is performed.

4. The system of claim 2 wherein the components, mounted one above the other on the assembly side, comprise:
    a lower fluid heating or cooling component,
    a center fluid distribution component and
    an upper individual fluid processing component,
    wherein the fluid heating or cooling component is operable to heat or cool the fluids in adjacent components, and
    the fluid distribution component is operable to individually supply and discharge fluid to and from the fluid processing component.

5. The system of claim 1, wherein at least one component is provided with at least one port for transferring fluids from one component to a directly adjacent component,
    the port establishing fluidic connection between the one component and the directly adjacent component when the components are mounted.

6. The system of claim 1 wherein at least one component is structured like a plate having at least one channel-like recess to conduct the fluids in at least one side parallel to the assembly side, and
    and the channel-like recess is covered by a directly adjacent component.

7. The system of claim 1 wherein the unit has a connection side operable to be connected to a connection side of an adjacent second unit to form a fluid bus.

8. The system of claim 1, wherein the unit has at least one locking device to interlock with an adjacent second unit.

9. The system of claim 6, wherein a sealing layer is provided between at least two adjacent components.

10. The system of claim 1, further comprising at least one data line and at least one corresponding data port.

11. The system of claim 1, further comprising at least one power line and at least one corresponding power port.

12. The system of claim 8, wherein the locking device is an electrical locking device.

13. A system for processing al least one fluid comprising:
    a unit for supplying and discharging the at least one fluid, the unit further having:
    at least one fluid line;
    at least one fluid port on an assembly side of the unit; and
    at least one device in which the fluid is processed,
    the one fluid line terminating in the one fluid port,
    the at least one device operable to be mounted on the assembly side and further operable to be coupled to the fluid port,
    the at least one device having at least on component performing at least one function related to the processing of the fluid, the component being mounted on the assembly side in one of a plurality of superimposed planes, and
    the fluid port supplying and discharging the fluid to and from the component, respectively, the fluid port further extending from the assembly side to the component,
    wherein at least one component which lies in one of the superimposed planes closer to the assembly side contains at least one passageway for at least one of the fluid ports for supplying and discharging fluids to and from a second component farther away from the assembly side.

* * * * *